United States Patent
Leonetti et al.

(10) Patent No.: US 9,574,198 B2
(45) Date of Patent: Feb. 21, 2017

(54) BACTERIA AND THE USES THEREOF

(71) Applicant: DEINOVE, Grabels (FR)

(72) Inventors: Jean-Paul Leonetti, Montpellier (FR); Juha-Pekka Pitkanen, Vantaa (FI); Paula Jouhten, Vantaa (FI)

(73) Assignee: DEINOVE, Grabels (FR)

( * ) Notice: Subject to any disclaimer, the term of this patent is extended or adjusted under 35 U.S.C. 154(b) by 0 days.

(21) Appl. No.: 14/366,333

(22) PCT Filed: Dec. 21, 2012

(86) PCT No.: PCT/EP2012/076577
§ 371 (c)(1),
(2) Date: Jun. 18, 2014

(87) PCT Pub. No.: WO2013/092967
PCT Pub. Date: Jun. 27, 2013

(65) Prior Publication Data
US 2014/0349338 A1 Nov. 27, 2014

Related U.S. Application Data

(60) Provisional application No. 61/579,821, filed on Dec. 23, 2011.

(30) Foreign Application Priority Data

Dec. 23, 2011 (EP) .................................... 11306768

(51) Int. Cl.
C12N 15/74 (2006.01)
C12N 1/08 (2006.01)
(Continued)

(52) U.S. Cl.
CPC ................. C12N 15/74 (2013.01); C12N 1/08 (2013.01); C12N 1/20 (2013.01); C12N 9/0006 (2013.01);
(Continued)

(58) Field of Classification Search
CPC ............ C12N 15/74; C12N 13/00; C12R 1/01
See application file for complete search history.

(56) References Cited

U.S. PATENT DOCUMENTS 5,439,803 A * 8/1995 Ross et al. ...................... 435/14
8,728,777 B2 5/2014 Biton et al.
(Continued)

FOREIGN PATENT DOCUMENTS

PT WO/2008/108674 * 9/2008
WO WO 2010/081899 7/2010
(Continued)

OTHER PUBLICATIONS

Emmerling et al., Metabolic Flux Responses to Pyruvate Kinase Knockout in *Escherichia coli.*, J. Bacteriol. (2002), vol. 184, No. 1, pp. 152-164.*

(Continued)

*Primary Examiner* — Alexander Kim
(74) *Attorney, Agent, or Firm* — Saliwanchik, Lloyd & Eisenschenk (57) ABSTRACT

The present invention relates to novel bacteria and the uses thereof. The invention particularly relates to bacteria having a metabolic pathway ratio between pentose phosphate and glycolysis greater than 0.5, and their uses in the chemical, pharmaceutical and agro-chemical industries, e.g., for producing compounds of industrial interest.

22 Claims, 2 Drawing Sheets

(51) Int. Cl.
| | |
|---|---|
| C12P 7/06 | (2006.01) |
| C12P 23/00 | (2006.01) |
| C12P 7/10 | (2006.01) |
| C12N 1/20 | (2006.01) |
| C12N 13/00 | (2006.01) |
| C12R 1/01 | (2006.01) |
| C12N 9/04 | (2006.01) |
| C12N 9/02 | (2006.01) |

(52) U.S. Cl.
CPC ............ *C12N 9/0042* (2013.01); *C12N 13/00* (2013.01); *C12P 7/065* (2013.01); *C12P 7/10* (2013.01); *C12P 23/00* (2013.01); *C12R 1/01* (2013.01); *Y02E 50/16* (2013.01); *Y02E 50/17* (2013.01)

(56) References Cited

U.S. PATENT DOCUMENTS

| | | |
|---|---|---|
| 2011/0294979 A1 | 12/2011 | Leonetti et al. |
| 2011/0306085 A1 | 12/2011 | Isop et al. |
| 2012/0058533 A1 | 3/2012 | Biton et al. |

FOREIGN PATENT DOCUMENTS

| | | |
|---|---|---|
| WO | WO 2010/094665 | 8/2010 |
| WO | WO 2010/130806 | 11/2010 |
| WO | WO 2010/130812 | 11/2010 |

OTHER PUBLICATIONS

Fujisaki et al., Isoprenoid synthesis in *Escherichia coli*. Separation and partial purification of four enzymes involved in the synthesis., J Biochem. (1986), vol. 99(5), pp. 327-1337.*

Nowicka et al., Occurrence, biosynthesis and function of isoprenoid quinones., Biochimica et Biophysica Acta (BBA)-Bioenergetics (Sep 2010), vol. 1797, Issue 9, pp. 1587-1605.*

Tian et al., Carotenoid 3',4'-desaturase is involved in carotenoid biosynthesis in the radioresistant bacterium Deinococcus radiodurans., Microbiology (2008), vol. 154, pp. 3697-3706.*

Sun et al., A novel carotenoid 1,2-hydratase (CruF) from two species of the non-photosynthetic bacterium Deinococcus., Microbiology (2009), vol. 155, pp. 2775-2738.*

Fuente-Hernández et al. (2013). Biofuels and Co-Products Out of Hemicelluloses, Liquid, Gaseous and Solid Biofuels—Conversion Techniques, Prof. Zhen Fang (Ed.), ISBN: 978-953-51-1050-7, InTech, DOI: 10.5772/52645, pp. 3-46.*

Ito et al., Isolation and Identification of Radiation-resistant Cocci Belonging to the Genus *Deinococcus* from Sewage Sludges and Animal Feeds., Agricultural and Biological Chemistry (1983), vol. 47:6, pp. 1239-1247.*

Zhang, Y.M. et al. "Induction of a Futile Embden-Meyerhof-Parnas Pathway in *Deinococcus radiodurans* by Mn: Possible Role of the Pentose Phosphate Pathway in Cell Survival" *Applied and Environmental Microbiology*, Jan. 1, 2000, pp. 105-112, vol. 66, No. 1.

Zhang, Y.M. et al. "Genetic Analysis of the Glucose Metabolic Enzymes of the Extremely Radioresistant *Deinococcus radiodurans*" Abstracts of the General Meeting of the American Society for Microbiology, 2000, p. 434, vol. 100.

Tian, B. et al. "Carotenoid biosynthesis in extremophilic Deinococcus-Thermus bacteria" *Trends in Microbiology*, Nov. 1, 2010, pp. 512-520, vol. 18, No. 11.

Obanye, A.I.C. et al. "Correlation between carbon flux through the pentose phosphate pathway and production of the antibiotic methylenomycin in *Streptomyces coelicolor* A3(2)" *Microbiology*, Jan. 1, 1996, pp. 133-137, vol. 142, No. 1.

Antoniewicz, M.R. et al. "Metabolic flux analysis in a nonstationary system: Fed-batch fermentation of a high yielding strain of *E. coli* producing 1,3-propanediol" *Metabolic Engineering*, May 1, 2007, pp. 277-292, vol. 9, No. 3.

Sauer, U. et al. "The Soluble and Membrane-bound Transhydrogenases UdhA and PntAB Have Divergent Functions in NADPH Metabolism of *Escherichia coli*" *The Journal of Biological Chemistry*, Feb. 20, 2004, pp. 6613-6619, vol. 279, No. 8.

Rauch, B. et al. "Characterization of enzymes involved in the central metabolism of *Gluconobacter oxydans*" Appl Microbiol Biotechnol., Jul. 30, 2010, pp. 711-718, vol. 88, No. 3.

Liedert, C. et al. "Physiology of Resistant *Deinococcus geothermalis* Bacterium Aerobically Cultivated in Low-Manganese Medium" *Journal of Bacteriology*, Mar. 1, 2012, pp. 1552-1561, vol. 194, No. 6.

Zhang, Y.-M. et al. "The DNA excision repair system of the highly radioresistant bacterium *Deinococcus radiodurans* is facilitated by the pentose phosphate pathway" *Molecular Microbiology*, Jun. 1, 2003, pp. 1317-1323, vol. 48, No. 5.

Obiero, J. etal. "Thioredoxin System from *Deinococcus radiodurans*" *Journal of Bacteriology*, Jan. 15, 2010, pp. 494-501, vol. 192, No. 2.

Written Opinion in International Application No. PCT/EP2012/076577, Apr. 16, 2013, pp. 1-9.

* cited by examiner

BACTERIA AND THE USES THEREOF

CROSS-REFERENCE TO RELATED APPLICATIONS

This application is the U.S. national stage application of International Patent Application No. PCT/EP2012/076577, filed Dec. 21, 2012, which claims the benefit of U.S. Provisional Patent Application No. 61/579,821, filed Dec. 23, 2011.

The Sequence Listing for this application is labeled "Seq-List.txt" which was created on Jun. 5, 2014 and is 11 KB. The entire contents of the sequence listing is incorporated herein by reference in its entirety.

The present invention relates to novel bacteria and the uses thereof. The invention particularly relates to bacteria having a particular metabolic profile and their uses in the chemical, pharmaceutical or agro-chemical industries, e.g., for producing metabolites or drugs of industrial interest.

BACKGROUND

Glucose is the major source of energy in cells. Bacteria typically use two metabolic pathways to catabolize glucose: the glycolysis and, to a lesser extent, the pentose phosphate pathway. Glycolysis converts glucose into pyruvate, and the free energy released is used to form ATP (adenosine triphosphate) and NADH (reduced nicotinamide adenine dinucleotide). The pentose phosphate pathway utilizes glucose to generate various substrates, and produces NADPH (reduced nicotinamide adenine dinucleotide phosphate) and pentoses. More specifically, the pentose phosphate pathway generates NADPH from NADP, in conjunction with the reduction of glucose-6-phosphate into ribulose-5-phosphate.

Although bacteria utilize mainly glycolysis to catabolize glucose, NADPH, which is produced during the pentose phosphate pathway, has a key role in biological reactions that lead to industrially useful compounds. Indeed, cells use NADPH as reducing equivalents for many biosynthetic and oxidation-reduction reactions involved in the protection against the toxicity of reactive oxygen species (ROS), allowing the regeneration of reduced glutathione. NADPH is also used in several important anabolic pathways, such as amino acid synthesis (e.g., arginine, proline, isoleucine, methionine, lysine), vitamin synthesis (e.g., pantothenate, phylloquinone, tocopherol), polyol synthesis (e.g., xylitol), isoprenoid synthesis, and fatty acid synthesis (including polyunsaturated fatty acids), as well as in the synthesis of other high added-value substances. In addition, NADPH is the source of reducing equivalents for cytochrome P450 hydroxylation of aromatic compounds, steroids, alcohols and drugs.

Because of the involvement of NADPH in the capacity of cells to conduct important enzymatic reactions, recombinant approaches have been proposed in the art to provide microorganisms with increased cellular NADPH.

For instance, attempts have been made to limit the activity of enzymes involved in the oxidation of NADPH, and/or to increase the activity of enzymes involved in the reduction of NADP. For example, U.S. patent application Ser. No. 10/577,084 relates to strains of microorganisms having one or more of their NADPH-oxidizing activities limited by a deletion of at least one gene coding for a quinine oxidoreductase or a soluble transhydrogenase.

U.S. Pat. No. 5,830,716 relates to a recombinant *Escherichia coli* expressing a nicotinamide dinucleotide transhydrogenase. In this bacterium, increased NADPH levels are produced from NADH.

Such approaches allow the production of modified microorganisms having an increased NADPH/NADP ratio. However, modifying the cell metabolism by deregulating specific genes is not entirely satisfactory. Indeed, the metabolic flux in such cells is not stable and cannot be controlled. Furthermore, the metabolic flux may not be adapted easily because the activity of such recombinant cofactor regeneration systems is strictly controlled by and dependent on the robustness of the bacteria physiology. In addition, the production of such recombinantly engineered organisms is costly and time-consuming, with repercussions on the production of the compounds of interest.

The over-expression of glucose-6-phosphate dehydrogenase to increase NADPH production has also been considered. However, over-expression of the corresponding coding gene is lethal for the cells.

There is therefore always a need for microorganisms suitable for producing industrially useful compounds. There is also a need for a source of reductive or anti-oxidant activity. There is also a need for improved methods for generating reduced compounds or anti-oxidant compositions.

SUMMARY OF THE INVENTION

The present invention describes the isolation and characterization of bacteria having particular metabolic profiles, which are particularly useful and advantageous for the production of high value compounds by biotransformation. More specifically, the invention reports the isolation and characterization of bacteria with a natural imbalance of their metabolism, which favours the pentose phosphate pathway. These bacteria can be used to produce valuable compounds, and also represent a potent antioxidant or reductive material.

An object of this invention more specifically relates to a bacterium which has a metabolic pathway ratio between pentose phosphate and glycolysis greater than 0.5. Preferred bacteria of this invention have a metabolic pathway ratio between pentose phosphate and glycolysis equal to or greater than 1, more preferably comprised between 1 and 20.

In a specific embodiment, the bacterium of the invention belongs to a *Deinococcus* species or a related bacterium.

Another object of the invention relates to a method for selecting or optimizing a bacterium, comprising the following steps:

a) providing a sample comprising bacteria;
b) subjecting the sample to a cell-destructing DNA damaging treatment, such as a repeated irradiation treatment;
c) identifying or isolating living or growing bacteria from said treated sample;
d) measuring the metabolic pathway ratio between pentose phosphate and glycolysis of bacteria of step c); and
e) selecting a bacterium of step d) which has a metabolic pathway ratio between pentose phosphate and glycolysis greater than 0.5, preferably equal to or greater than 1, even more preferably comprised between 1 and 20.

In a particular embodiment, the treatment of step b) comprises repeated UV irradiation, particularly a sequential UV treatment, e.g., a repetition of at least 2, preferably 3 or more irradiations at essentially regular intervals.

The invention further relates to a bacterium as defined above, further comprising at least one recombinant nucleic acid sequence. Preferentially, the at least one recombinant nucleic acid sequence encodes an NADPH-dependent enzyme able to catalyze a reaction of interest, such as an NADPH-dependent alcohol dehydrogenase or a cytochrome P450 enzyme.

A further object of the invention relates to the use of at least one nucleic acid sequence of a bacterium as defined above, encoding a NADPH-dependent enzyme, to transform a microorganism, particularly a bacterium or a yeast, to provide a recombinant microorganism with a metabolic pathway ratio between pentose phosphate and glycolysis greater than 0.5. The invention further relates to such a microorganism.

A further object of the invention relates to a co-culture of at least two distinct microorganisms, wherein at least one of said microorganisms is a bacterium as defined above, and at least one of said microorganisms is a prokaryotic or eukaryotic cell, preferably a yeast, and wherein said at least two microorganisms are symbiotic to each other.

A further object of the invention relates to a cell-free extract of a bacterium as defined above, preferably selected from a cell supernatant, cell debris, cell walls, and DNA extract.

A further object of the invention relates to the use of a bacterium or extract as defined above in a bioproduction process.

A further object of the invention relates to the use of a bacterium or extract as defined above for the production of a compound of interest, particularly a metabolite and/or drug.

A further object of the invention relates to the use of a bacterium or extract as defined above for the bioconversion of a substrate into a substance of interest.

A further object of the invention relates to the use of a bacterium or extract thereof as defined above for the production of a reduced or antioxidant molecule or composition.

A further object of the invention relates to a process for the bioproduction of a compound of interest, the process comprising producing the compound with a bacterium of the invention or an extract thereof and, optionally, recovering the compound. In a particular embodiment, the process comprises exposing a substrate to such a bacterium or extract, the substrate being converted by said bacterium or extract into a compound of interest. In another embodiment, the process comprises exposing the bacterium or extract to a carbon source, the bacterium or extract producing the compound by fermentation of said carbon source.

The compound of interest may be any organic compound such as a protein, peptide, lipid, nucleic acid, organic acid, alcohol, amino acid, etc. The compound may be a drug, metabolite, or fine chemical product such as biofuel, bioplastic, dye, etc. The compound may be in purified form, or a mixed preparation.

In this regard, a further object of the invention relates to a method for the production of a metabolite and/or drug of interest, the method comprising culturing a bacterium as defined above which produces said metabolite and/or drug in an appropriate culture medium, and recovering the metabolite and/or drug of interest from the culture medium.

A further object of the invention relates to a method for the bioconversion of a substrate into a substance of interest, the method comprising culturing a bacterium as defined above having the bioconversion activity in an appropriate culture medium comprising a source of carbon and the substrate under conditions allowing bioconversion, and recovering the substance of interest from the culture medium.

A further object of the invention relates to a method for the production of a reduced molecule of interest, the method comprising culturing a bacterium as defined above which produces said reduced molecule in an appropriate culture medium comprising a source of carbon, and recovering the reduced molecule of interest from the culture medium. Such reduced molecules can be used as an active ingredient for the preparation of a dietary supplement and/or for the preparation of a cosmetic composition with antioxidant properties.

A further object of the invention is a dietary supplement or a cosmetic composition comprising a bacterium of the invention or an extract thereof.

A further object of the invention resides in a composition comprising a bacterium of the invention or an extract thereof, for use as an anti-oxidant.

DETAILED DESCRIPTION OF THE INVENTION

Figure 1:
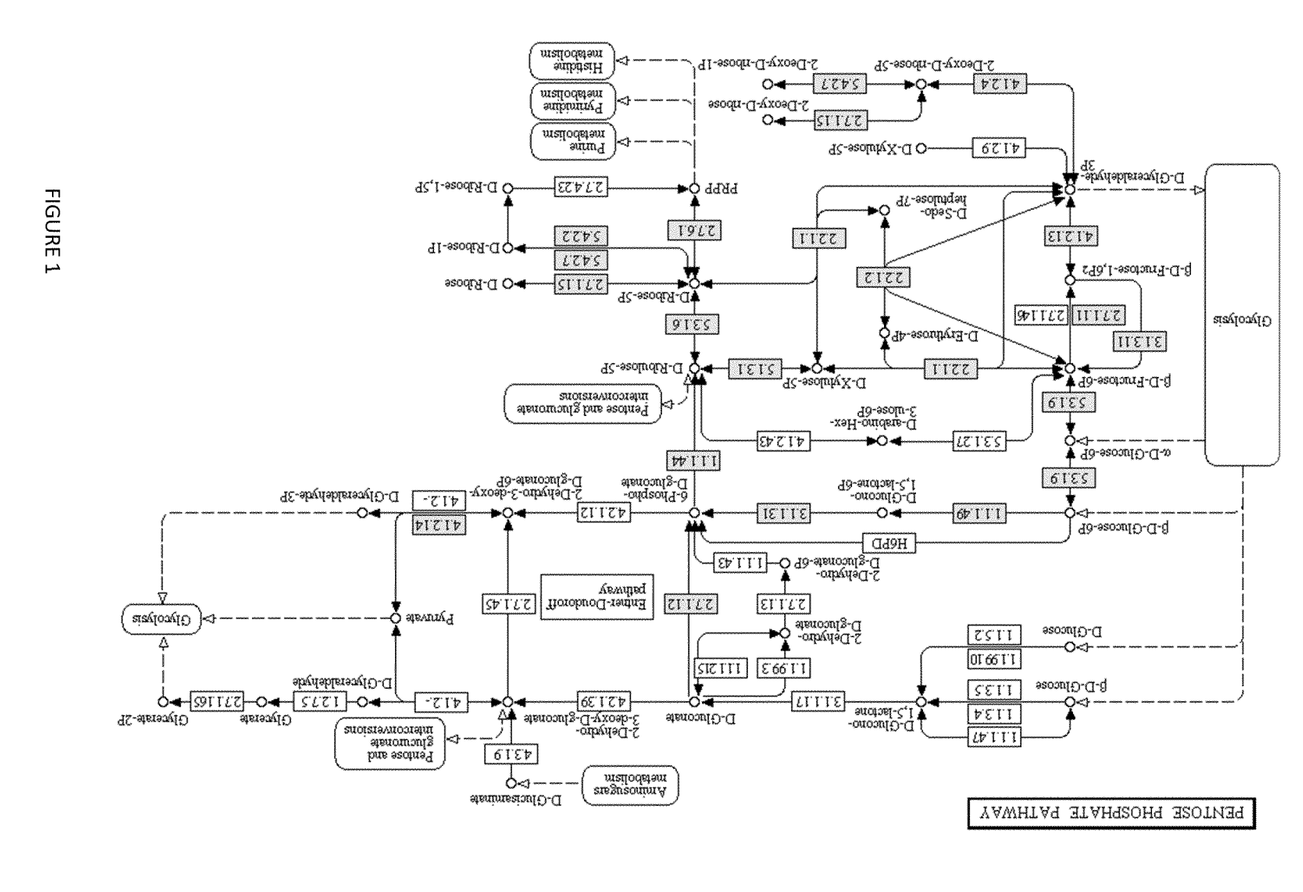
FIG. 1: Schematic representation of the pentose phosphate and the glycolysis pathways.
Figure 2:
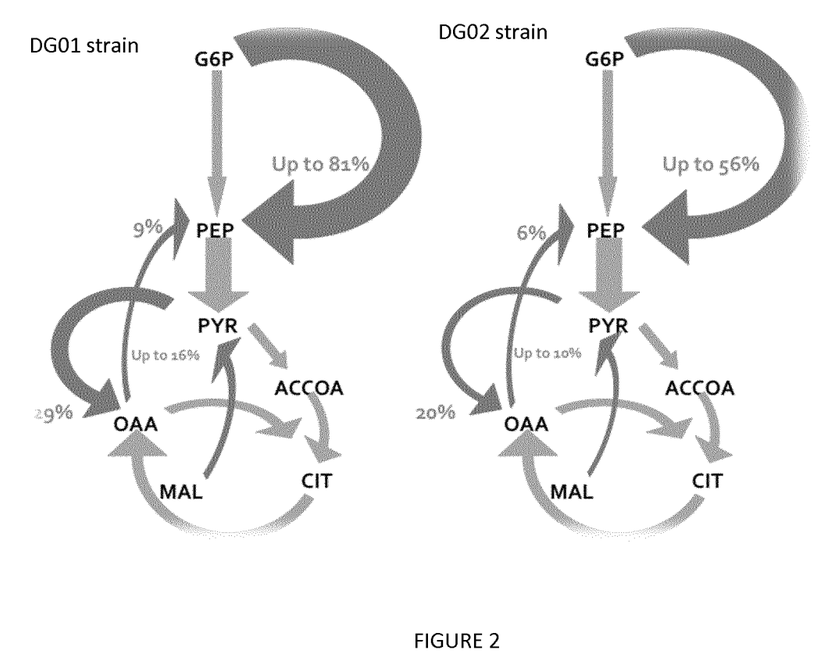
FIG. 2: Schematic representation of the main metabolic flux ratios in two strains of *Deinococcus*, showing that the flux through the oxidative pentose phosphate pathway in both strains is substantially high (superior to 1). Similarly, the anaplerotic flux from pyruvate to oxaloacetate and malic enzyme flux from malate to pyruvate is high in both strains.

The invention relates, generally, to bacteria having a permanent and high metabolic flux through the oxidative pentose phosphate pathway, as well as to their uses for producing substances with NADPH-consuming biosynthesis routes. The bacteria according to the invention can be used in NADPH-consuming biotransformation processes, including fermentation and bioconversion processes. The present invention also concerns methods for the preparation of substances by biotransformation, through growth in an appropriate medium of a bacterium according to the invention. The invention further concerns recombinant bacteria, which are optimized to include genetic elements necessary for the preparation of such substances.

DEFINITIONS

In the context of the invention, the term "*Deinococcus*" bacteria includes wild type or natural variant strains of *Deinococcus*, e.g., strains obtained through accelerated evolution, by DNA-shuffling technologies, or recombinant strains obtained by insertion of eukaryotic, prokaryotic and/or synthetic nucleic acid(s). *Deinococcus* bacteria can designate any bacterium of the genus *Deinococcus*, such as, without limitation, a *D. geothermalis, D. cellulolysiticus, D. radiodurans, D. proteolyticus, D. radiopugnans, D. radiophilus, D. grandis, D. indicus, D. frigens, D. saxicola, D. maricopensis, D. marmoris, D. deserti, D. murrayi, D. aerius, D. aerolatus, D. aerophilus, D. aetherius, D. alpinitundrae, D. altitudinis, D. apachensis, D. aquaticus, D. aquatilis, D. aquiradiocola, D. aquivivus, D. caeni, D. claudionis, D. ficus, D. gobiensis, D. hohokamensis, D. hopiensis, D. misasensis, D. navajonensis, D. papagonensis, D. peraridilitoris, D. pimensis, D. piscis, D. radiomollis, D. roseus, D. sonorensis, D. wulumuqiensis, D. xibeiensis, D.*

*xinjiangensis, D. yavapaiensis* or *D. yunweiensis* bacterium. Preferred *Deinococcus* bacteria are *D. geothermalis, D. cellulolysiticus, D. deserti, D. murrayi*, and *D. radiodurans*.

A bacterium "related" to *Deinococcus* designates a bacterium which (i) contains a 16S rDNA which, upon amplification using primers GTTACCCGGAAT-CACTGGGCGTA (SEQ ID NO: 1) and GGTATCTACGCATTCCACCGCTA (SEQ ID NO: 2), generates a fragment of about 158 base pairs and/or (ii) resists a UV treatment of 4 mJ/cm². In a particular embodiment, *Deinococcus*-related bacteria are bacteria having a 16S rDNA molecule which is at least 70%, preferably at least 80% identical in sequence to a *Deinococcus* 16S rDNA sequence.

In the context of the invention, the term "bioproduction" designates any production process that uses a microorganism, or an extract or isolated part thereof.

In the context of the invention, the term "fermentation" designates a process during which a substance is produced by a microorganism from a carbon source. Preferred fermentation processes of the invention involve at least one NADPH-dependent step.

In the context of the invention, the term "bioconversion" is the action mediated by a bacterium or an extract thereof for converting a given substrate into a substance of interest. The substrate is usually not assimilated by the bacterium and distinct from the carbon source. Preferred bioconversion processes of the invention include at least one NADPH-dependent step.

The term "NADPH-dependent" indicates that a process or reaction involves at least one enzyme whose activation or activity requires or consumes NADPH.

A "gene" designates any nucleic acid encoding a protein. The term gene encompasses DNA, such as cDNA or gDNA, as well as RNA. The gene may be first prepared by, e.g., recombinant, enzymatic and/or chemical techniques, and subsequently replicated in a host cell or an in vitro system. The gene typically comprises an open reading frame encoding a desired protein. The gene may contain additional sequences such as a transcription terminator, a signal peptide, an IRES, an intron, etc. Preferably, the gene does not contain an intron.

The term "reconstructed" or "recombinant", in relation to a sequence, nucleic acid, or unit in a bacterium, indicates a sequence, nucleic acid or unit which does not exist naturally in the bacterium and has been assembled and/or inserted in said bacterium or an ancestor thereof. The term "reconstructed" or "recombinant", in relation to a bacterium, indicates a bacterium which does not exist naturally and wherein a sequence, nucleic acid or unit has been assembled and/or inserted in said bacterium or an ancestor thereof.

A "cell-destructing DNA damaging treatment" indicates a treatment that is sufficient to cause 90% cell death, or more, in a culture of *E. coli* bacteria. Even more preferably, the cell-destructing DNA damaging treatment is a treatment that is sufficient to reduce by at least 2 log the bacterial titer in a culture of *E. coli*. Examples of such treatments include irradiation, preferably repeated and sequential UV irradiation, and/or the use of genotoxic agents. A preferred stress treatment is a UV treatment of between 0.5 and 400 mJ/cm², more preferably of between 1 and 200 mJ/cm², typically between 1 and 100 mJ/cm², applied for a period of time of about 5" to 5'. A preferred UV treatment is 4 mJ/cm² for 30 seconds, which may be repeated at an interval of between 1 and 8 hours, preferably 3 to 5 hours, and more preferably of about 4 hours. Specific cell stress treatments according to the invention have been described in patent application EP2210935, which is incorporated therein by reference.

An "extract of bacteria" refers to material obtained, e.g., following lysis of bacteria. The extract of bacteria comprises at least part of dyed bacteria, such as DNA, cell wall fragments, enzymes and/or metabolites, etc. The extract may further comprise the culture medium wherein the bacteria have excreted enzymes, metabolites, etc. The extract may contain solely enzyme(s) of particular interest, produced by said bacteria. The extract may be obtained using any method suitable for lysing bacteria. For example, the extract may be obtained by lysing bacterial cells under basic conditions (e.g., by means of an organic or inorganic base). Mechanical methods of lysing bacterial cells may be used too, such as vortex. If required, the extract may be filtered by passage through one or more microfilters or ultrafilters before use, for example in order to remove cell wall fragments from the bacterial extract. The extract may be in liquid or solid form. In a particular embodiment, the extract is lyophilised and conditioned in powder form.

Bacteria with Increased Pentose Phosphate Pathway

The invention stems from the identification of bacteria having a surprisingly high and permanent pentose phosphate pathway flux.

The pentose phosphate pathway (abbreviated as "PP pathway") refers to a cell process that converts glucose molecules into biochemically useful smaller molecules and generates NADPH. The PP pathway comprises two distinct phases. During a first, oxidative phase NADPH and ribulose-5-P are generated from glucose. The oxidative phase can be represented by the following chemical reaction:

Glucose-6-phosphate+2 NADP$^+$+H$_2$O→ribulose-5-phosphate+2 NADPH+2H$^+$+CO$_2$.

The second phase, which is non-oxidative, allows the conversion of ribulose-5-phosphate into various substrates, particularly for the construction of nucleotides and nucleic acids. The NADPH generated during the PP pathway is an important cofactor for reductive biosynthesis reactions within the cells. For example, NADPH provides reducing equivalents for cytochrome P450 hydroxylation of aromatic compounds, steroids or alcohols, and for various biosynthetic reactions, including fatty acid chain elongation, and lipid or isoprenoid synthesis. Additionally, NADPH provides reducing equivalents for oxidation reduction involved in protection against the toxicity of reactive oxygen species.

The inventors have discovered and isolated a class of bacteria having a surprising and remarkably high PP pathway flux at least during the exponential phase. More particularly, in these bacteria, an important part of glucose is naturally catabolized through the PP pathway, leading to the permanent (e.g., continuous) production of an important amount of NADPH. Bacteria having a flux ratio of pentose phosphate/glycolysis above 0.5 have been selected, and their growth capacity and production ability have been verified by the inventors, confirming their remarkable utility in bioproduction.

An object of the invention therefore resides in a bacterium, wherein said bacterium has a metabolic pathway ratio between pentose phosphate and glycolysis (herein after PP/G) greater than 0.5.

Such an imbalance of the metabolic pathways is particularly surprising and unprecedented. Indeed, up to now, it was commonly accepted that microorganisms very preferentially use glycolysis for degrading glucose. For example, the innate metabolic pathway ratio of pentose phosphate/glycolysis for *Escherichia coli* is inferior to 0.33 in the exponential phase (Maciek R. Antoniewicz et al Metab Eng. 2007 May; 9(3): 277-292). In *Saccharomyces cerevisiae*, this ratio is about 0.25 (Paula Jouhten et al BMC Syst Biol. 2008; 2: 60; van Winden WAFEMS Yeast Res. 2005 April; 5(6-7): 559-68), and for *Bacillus subtillis* 0.2 (Dauner M Appl Environ Microbiol. 2002 April; 68(4):1760-71). The invention now discloses a class of bacteria having a PP/G ratio above 0.5. The present invention even discloses the identification of bacteria with a PP/G ratio above 1, 2, 3, 5, 10 or even 15. In such bacteria, the PP pathway is highly predominant and most glucose is consumed by the pentose phosphate route, the glycolysis being very limited.

Furthermore, in the bacteria of the invention, the high PP/G metabolic ratio is permanent during the exponential phase, i.e., it is not conditioned by specific culture conditions (e.g., a high oxidative stress).

The present invention therefore relates to these bacteria, methods for their isolation and culture, as well as to the uses thereof, particularly in the chemical, pharmaceutical and agro-chemical industries, e.g., to produce, by biotransformation, substances with NADPH-consuming biosynthesis routes.

In the context of the invention, a bacterium having a "a metabolic pathway ratio between pentose phosphate and glycolysis greater than 0.5" designates a bacterium wherein more than one third of the glucose is consumed through the pentose phosphate pathway and the remainder is consumed by glycolysis. When the ratio is equal to or greater than 1, this indicates that at least 50% of the glucose is consumed by said bacterium by the PP pathway.

Preferred bacteria of the invention have a PP/G ratio greater than 2, 2.5, 3, 3.5, 4, or 5.

In a particular embodiment, bacteria of the invention have a metabolic pathway ratio between pentose phosphate and glycolysis between 1 and 20, preferably between 2 and 20. As detailed in the experimental section, the inventors have been able to identify and cultivate bacteria with a PP/G ratio as high as 19, which means bacteria wherein 95% of the glucose consumed is degraded using the pentose phosphate pathway. The inventors show these bacteria are viable, can grow under industrially-compatible culture conditions and exhibit improved properties for bioproduction processes.

In another particular embodiment, bacteria of the invention have a PP/G ratio comprised between 2 and 10. Specific examples of bacteria of the invention as disclosed in the examples have a PP/G ratio of 1.2, 2.3, 5.6, 9, and 19. More particularly, *Deinococcus* strain DG01 as disclosed in the examples has a PP/G ratio of 1.2. *Deinococcus* strain DG02 as disclosed in the examples has a PP/G ratio of 19.

The bacteria of the invention, with increased metabolic pentose phosphate pathway, can be identified and selected using any techniques suitable for measuring metabolic flux distributions. In this regard, an object of the invention also relates to a method for selecting or optimizing a bacterium, comprising the following steps:
   a) providing a sample comprising bacteria, preferably a sample comprising uncharacterized bacteria;
   d) measuring the metabolic pathway ratio between pentose phosphate and glycolysis of bacteria in the sample; and
   e) selecting a bacterium of step d) which has a metabolic pathway ratio between Pentose phosphate and glycolysis greater than 0.5.

The metabolic pathway ratio can be measured by measurement of isotope incorporation into intracellular pools of specific metabolites, preferentially of low abundant metabolites.

For example, the PP/G ratio can be evaluated by measuring isotope incorporation into a metabolite characteristic of the PP or G pathway. The % incorporation obtained is directly correlated to the % usage of the corresponding metabolic pathway.

A specific example of a suitable method is based on a measure of isotope incorporation into glyceraldehyde-3-phosphate (G3P), or a derivative thereof such as serine (see the experimental section, as well as, e.g., Krömer et al., "$^{13}C$-fluxomics: a tool for measuring Metabolic phenotypes", Australian Biochemist, Vol 40, No 3, December 2009, pp. 17-20). Indeed, the $C_1$ carbon atom of glucose is transferred to G3P during glycolysis while, in the first step of the PP pathway, $C_1$ of glucose-6-phosphate is lost to $CO_2$. Accordingly, no label is retained if glucose-6-phosphate, labeled at $C_1$ position, is catabolized via the PP pathway, while the label is retained through glycolysis, and one mole labeled glucose-6-phosphate gives one mole labeled glyceraldehyde-3-phosphate.

Accordingly, in a particular embodiment, step d) of the process comprises:
   Culturing the bacteria in a culture medium comprising glucose labeled at $C_1$ position as a source of carbon, under conditions allowing the growth of bacteria;
   Recovering and lysing the bacteria; and
   Measuring the label incorporation in glyceraldehyde-3-phosphate or a derivative thereof, and using such incorporation to calculate the PP/G ratio.

The label used is typically a radiolabel, such as e.g., $^{13}C$.

Further techniques to calculate the PP/G ratio include mass spectrometry, to measure specific metabolites or fluxes, or proteomics.

In an embodiment of the invention, the bacteria are obtained or selected by a process comprising:
   a) providing a sample comprising bacteria, particularly a sample comprising uncharacterized bacteria;
   b) subjecting the sample to a cell-destructing DNA damaging treatment, such as a repeated irradiation treatment;
   c) identifying or isolating living or growing bacteria from said treated sample;
   d) measuring the metabolic pathway ratio between pentose phosphate and glycolysis of such bacteria, for example by using the $^{13}C$ metabolic flux analysis as described above; and
   e) selecting bacteria which have a metabolic pathway ratio between pentose phosphate and glycolysis greater than 0.5, preferably greater than 1.

The starting sample may comprise bacteria of any genus or species, in particular uncharacterized or unknown bacteria. The repeated irradiation treatment is typically a UV treatment of between 0.5 and 400 mJ/cm$^2$, more preferably of between 1 and 200 mJ/cm$^2$, typically between 1 and 100 mJ/cm$^2$, applied for a period of time of about 5" to 5', which may be repeated at an interval of between 1 and 8 hours, preferably 3 to 5 hours, and more preferably of about 4 hours. A preferred UV treatment is 4 mJ/cm$^2$ for 30 seconds, repeated at an interval of 4 hours.

The invention also relates to bacteria identified or obtainable by the above methods. As shown in the examples, preferred bacteria of the invention are *Deinococcus* or related bacteria. *Deinococcus* is a gram-positive bacterium that was isolated in 1956 by Anderson and collaborators. This extremophile organism is resistant to DNA damage by UV and ionizing radiations or by cross-linking agent (mitomycin C) and is tolerant to desiccation. WO2009/063079 shows that *Deinococcus* bacteria can resist solvents and transform biomass to generate ethanol. WO2010/130806 further discloses recombinant *Deinococcus* strains wherein ethanol biosynthesis genes have been inserted. The invention now shows that *Deinococcus* or related bacteria may be isolated, having a permanent PP/G ratio of at least 0.5. These bacteria represent a highly valuable biocatalyst for bioproduction processes, as well as for the production of antioxidant compositions.

The invention also relates to a method of conducting a bioproduction process, the method comprising testing whether the PP/G ratio of the microorganism used to verify the ratio is equal to or greater than 0.5.

The bacteria of the invention present a substantial advantage over the prior art in that they have a natural elevated PP/G ratio. As mentioned above, some bacteria may have been engineered to increase their NADPH production. However, these bacteria contain inserted nucleic acids, which may confer instability or non-compliance with regulatory guidelines. The bacteria of the invention have a natural and permanent elevated PP/G ratio, and such permanent ratio is not caused by expression of a recombinant nucleic acid. The elevated ratio is permanent in that it is not subject to specific culture or stress conditions. While the ratio may vary in the cells of the invention depending on certain conditions, the basal ratio remains greater than 0.5.

The bacteria of the invention can be grown in specific and/or optimized culture media. Preferentially, the culture medium contains at least lignin, cellulose, hemi-cellulose, starch, xylane, polysaccharide, xylose, sucrose, glucose, galactose, lactose, molasses, or derivatives thereof, as a carbon source. Starch refers to a carbohydrate consisting of a large number of glucose units joined together by 1-4 and 1-6 glycosidic bonds. Starch is an energy storage molecule accumulated by many plants and bacteria, and starch molecules arrange themselves in the plant in semi-crystalline granules. A simple source of carbon that is especially preferred is glucose.

The culture medium can also contain one or more substances (e.g. amino acids, vitamins or mineral salts) that favour the growth of the bacteria and/or the production/bioconversion of substances of interest. In the case of bioconversion, the process also includes the addition to the appropriate culture medium of the substrate that is to be converted. The optimized conditions to favour the growth of the bacteria are set by those skilled in the art. In the same way, those skilled in the art know the nature of the substrates and/or of the carbon sources required in the culture medium to obtain the desired substances. These requirements are documented and can be easily implemented by those skilled in the art.

For example, manganese can be added to the culture medium for improving the incorporation of xylose and galactose in glycoproteins. In addition manganese acts as a catalyst and cofactor in many enzymatic processes involved in the synthesis of fatty acids and cholesterol. Otherwise, by depleting the culture medium of manganese, it is possible to further decrease the glycolysis. Indeed, manganese is involved in the transfer of high-energy phosphate groups by phosphotransferase enzymes, which are involved in several steps of glycolysis.

A particular object of the invention resides in a composition comprising a culture of bacteria as defined above. In a preferred embodiment, the composition is devoid of cells having a PP/G ratio below 0.5.

Bioproduction Process

Because of their potent metabolic profile, the bacteria of the invention can be used efficiently in bioproduction processes for producing substances of interest, such as metabolites, drugs, reduced molecules, or antioxidant molecules or compositions.

In this regard, an object of the invention resides in a bioproduction process for the production of a molecule, wherein the process utilizes a bacterium having a PP/G ratio of at least 0.5, or an extract thereof.

A further object of the invention relates to a process for the bioproduction of a compound, the process comprising producing the compound with a bacterium of the invention or an extract thereof and, optionally, recovering the compound. In a particular embodiment, the process comprises exposing a substrate to such a bacterium or extract, the substrate being converted by said bacterium or extract into a compound of interest. In another embodiment, the process comprises exposing the bacterium or extract thereof to a carbon source, the bacterium or extract producing the compound by fermentation of said carbon source.

The compound of interest may be any organic compound such as a protein, peptide, lipid, nucleic acid, organic acid, alcohol, amino acid, etc. The compound may be a drug, metabolite, or fine chemical product. The compound may be in purified form, or a mixed preparation.

In this regard, a further object of the invention relates to a method for the production of a metabolite and/or drug of interest, the method comprising culturing a bacterium as defined above which produces said metabolite and/or drug in an appropriate culture medium, and recovering the metabolite and/or drug of interest from the culture medium. The process is preferably an NADPH-dependent process.

A further object of the invention relates to a method for the bioconversion of a substrate into a substance of interest, the method comprising culturing a bacterium as defined above having the bioconversion activity in an appropriate culture medium comprising a source of carbon and the substrate under conditions allowing bioconversion, and recovering the substance of interest from the culture medium. The process is preferably an NADPH-dependent process.

A further object of the invention relates to a method for the production of a reduced molecule of interest, the method comprising culturing a bacterium as defined above which produces said reduced molecule in an appropriate culture medium comprising a source of carbon, and recovering the reduced molecule of interest from the culture medium. Such reduced molecules can be used as an active ingredient for the preparation of a dietary supplement and/or for the preparation of a cosmetic composition with antioxidant properties. The process is preferably an NADPH dependent process.

The term "metabolite" designates all possible intermediate molecules generated during a fermentation process, including but not limited to chemical products of industrial interest, such polyols, alcohols, dicarboxylic acids, amino acids, vitamins, sterols, lipids including isoprenoids, flavonoids, fatty acids, and building blocks. The metabolites may also have utility in cosmetics or agriculture, such as pigments, insecticides, pesticides, chemical-degrading compounds, etc.

The term "drug" designates, generally, any compound having a biological activity. This term includes any protein, polypeptide, peptide, chemical compound, lipid, saccharide, etc. having a biological activity which may be used in the human or veterinary pharmaceutical industry. Examples of such drugs include, without limitation, antibiotics, hormones, bacteriostatic compounds, anti-metabolite agents, antioxidant agents, chemotherapeutic compounds, anti-fungal agents, anti-viral compounds, cytokine-activity compounds, cell-growth factors, vaccines and adjuvants.

The term "reduced molecule" or "reduced agent" designates, generally, a molecule capable of inhibiting the oxidation of other molecules by promoting its own oxidation (i.e., it donates an electron to another compound in a reduction-oxidation reaction) in response to an oxidative insult. Such reduced molecules present an anti-oxidative activity suitable for reducing the production of reactive oxygen species (ROS). Because ROS can interact with a large number of molecules including other small inorganic molecules as well as DNA, proteins, lipids, carbohydrates and nucleic acids, the use of reduced molecules of the invention in a cosmetic composition and/or a dietary supplement can contribute to decreasing the intracellular ROS level and so to decreasing the cellular damages mediated by ROS.

The term "alcohol" or "bioalcohol" more specifically designates a linear or branched alcohol, diol or triol comprising from 1 and 5 carbon atoms, preferably from 1 to 4 carbon atoms. Specific and preferred examples of "alcohols" include $C_{1-4}$ alcohols selected from methanol, ethanol, propanol, isopropanol, propanediol, butanol, 2,3-butanediol, 1,4-butanediol, isobutanol, or glycerol, more preferably ethanol.

Polyols are alcohols containing multiple hydroxyl groups. The sugar alcohols are useful compounds in the food industry, used for example for increasing the palatability of food or beverages. In particular, the methods of the invention allow the production of maltitol, sorbitol, xylitol and isomalt. The polymeric polyols can be used in polymer chemistry as reactants to make other polymers. For examples, polymeric polyols can be reacted with isocyanates to make polyurethanes.

Examples of amino acids include, without limitation, lysine, methionine, threonine, proline, glutamic acid, homoserine, isoleucine, and valine.

Vitamins which can be produced using bacteria or methods of the invention include pantoate, trans-neurosporene, phylloquinone and tocopherols.

Examples of sterols which can be obtained using bacteria or methods of the invention include steroid compounds with long (8-10 carbons) aliphatic side-chains (usually at position 17) and at least one alcoholic hydroxyl group, usually at position 3. In particular, the methods of the invention allow the production of squalene, cholesterol, testosterone, progesterone and cortisone. Sterols and related compounds play essential roles in the physiology of animals. For example, cholesterol affects the cell membrane's fluidity and serves as a secondary messenger in developmental signaling. Corticosteroids, such as cortisol, act as signaling compounds in cellular communication and general metabolism.

Flavonoids generally refer to ketone-containing compounds. Flavonoids have an antioxidant activity similar to the antioxidant activity of vitamin C. Flavonoids can also have anti-allergic, anti-inflammatory, anti-cancer, and anti-diarrheal activities. In particular, the methods of the invention allow the production of quercetin and epicatechin. Such flavonoids can be obtained by using recombinant bacteria of the invention.

The bacteria and methods of the invention can also be used for the production of dicarboxylic acids, and preferentially C5-C30 dicarboxylic acids, having the general formula HOOC—$(CH_2)_n$—COOH. They are particularly suited to produce saturated dicarboxylic acids (e.g., glutaric acid, adipic acid, pimelic acid, suberic acid, azelaic acid, sebacic acid), aromatic dicarboxylic acids (e.g., phthalic acid, isophthalic acid, terephthalic acid) and unsaturated dicarboxylic acids (e.g., glutaronic acid, traumatic acid, muconic acid). Dicarboxylic acids are suitable substrates for preparation of organic acids for the pharmaceutical and food industries. Furthermore, they are useful materials for the preparation of fragrances, polyamides, adhesives, lubricants, and polyesters. In specific embodiments, dicarboxylic acids can be obtained by using a recombinant bacterium of the invention comprising a recombinant cytochrome P450.

In the context of the invention, fatty acids include both saturated and unsaturated fatty acids, with long aliphatic chains (i.e. aliphatic tails longer than 6 carbons). In particular, the methods of the invention allow the production of capric acid, myristic acid, palmitic acid and lignoceric acid (saturated fatty acids) and of palmitoleic acid, oleic acid, linoleic acid and erucic acid (insaturated fatty acids).

The methods of the invention may also be used to produce lipids, particularly isoprenoids. Indeed, isoprenoid biosynthesis starts from both isopentenyl diphosphate (IPP) and dimethylallyl pyrophosphate (DMAPP). One pathway for synthesizing IPP and DMAPP comprises the production of mevalonate (MEP) from pyruvate. This reaction requires the use of 1-deoxy-D-xylulose-5-phosphate reductoisomerase, which is an NADPH-dependent enzyme. Isoprenoids are useful for diverse applications such as biofuels, pigments, antioxidants, flavors, or in the pharmaceutical field.

In a particular embodiment, the method of the invention is used to produce carotenoids. Carotenoids have many physiological functions, most of them having an antioxidant activity. Furthermore, the products of degradation of carotenoid (e.g., ionones, damascones and damascenones) are useful materials for the preparation of perfumes and more generally in the fragrance industry.

In a particular embodiment, the method of the invention is used to produce biofuel. The term biofuel according to the invention comprises "first generation biofuel" and/or "second generation biofuel". First generation biofuels are obtained from vegetable or animal organic material, preferably from sugar, starch, vegetable oil or animal fats. The main source for the production of first generation biofuels is edible plants or parts thereof. First generation biofuels include vegetable oil, biodiesel, bioalcohols, biogas, syngas and solid biofuels. Bioalcohols include ethanol, propanol and butanol. Second generation biofuels are produced preferably from non-edible plants or non-edible parts of plants. They include non-food crops, biomass wastes, stalks of wheat, corn and wood.

Reactors

In particular embodiments, the methods of the invention are performed in reactors. By "reactor" is meant a conventional tank or any apparatus or system for fermentation and/or bioconversion, typically selected from bioreactors, biofilters, rotary biological contactors, and other gaseous and/or liquid phase bioreactors. The apparatus which can be used according to the invention can be used continuously or in batch loads.

In the reactor, to implement the method of the invention, at least one bacterium or bacterial extract of the invention is used, while said reactor is arranged and supplied so that physicochemical conditions are set up and maintained therein so that said bacterium is operational. Depending on the bacterium used, the method may be conducted under aerobiosis, anaerobiosis or microaerobiosis. The process of the invention may thus preferably be performed at a temperature of about 40° C. or more, particularly a temperature comprised between 40 and 70° C., under acid pH conditions, and/or in the presence of ethanol.

Recombinant Bacterium

In order to improve their performances or to confer new activities, the bacteria of the invention may be modified to contain one or several recombinant genes. They are particularly suited to contain and express recombinant genes encoding NADPH-dependent enzymes.

In a specific embodiment, a bacterium of the invention comprises a recombinant nucleic acid sequence encoding an NADPH-dependent alcohol dehydrogenase. Such a bacterium can be used for producing ethanol, by growing this bacterium in a culture medium comprising for example glucose as a carbon source.

For example, strain DG03 as disclosed in the experimental section has been engineered in order to contain an NADPH-dependent alcohol dehydrogenase encoding gene from *Moorella* sp. HUC 22-1 into its chromosome (SEQ ID NO: 3). The expression of this gene confers a particular advantage on the bacterium for the production of bioethanol.

In another specific embodiment, a bacterium of the invention comprises a recombinant cytochrome P450. Such a bacterium can be used for bioconverting fatty acids into w-alcohols and corresponding dicarboxylic acids. More precisely, the recombinant cytochrome P450 catalyzes the required oxidation of the fatty acids for obtaining corresponding dicarboxylic acids. The recombinant bacterium is for example cultivated in a culture medium comprising a carbon source and the fatty acids to be bioconverted.

For example, a *Deinococcus* of the invention, having a natural and permanent PP/G ratio of at least 0.5, may be engineered in order to contain an NADPH-dependent cytochrome P450 encoding gene from *Bacillus megaterium* (P450BM-3(CYP102A1)) into its chromosome (SEQ ID NO: 4). The expression of this gene confers a particular advantage on the bacterium for the bioconversion of fatty acids.

A recombinant gene or nucleic acid may be inserted into the genome of the bacterium, or inserted as (autonomously) replicating molecules, e.g., on a plasmid, episome, artificial chromosome, etc., as disclosed above. In a preferred embodiment, the recombinant nucleic acid is inserted in the genome of said bacterium in replacement of an endogenous gene. Expression of the expressed recombinant genes may be verified using, e.g., quantitative PCR, Western blot or by enzymatic assays known per se in the art.

According to an embodiment of the invention, at least one nucleic acid sequence of a bacterium of the invention, encoding an NADPH-dependent enzyme, is used to transform a microorganism, such as a bacterium or a yeast, to provide a recombinant microorganism with a metabolic pathway ratio between pentose phosphate and glycolysis greater than 0.5.

Alternatively or in addition, the bacterium of the invention can be further modified to delete glycolysis genes. For example, a bacterium of the invention has at least one disrupted gene among the phosphoglucose isomerase, the G6P dehydrogenase and both pyruvate kinase isoenzymes. The resulting recombinant bacterium uses further the PP pathway as the primary route of glucose catabolism. For example, a recombinant bacterium having both pyruvate kinase isoenzymes disrupted reroutes its metabolic flux via the combined reactions of phosphoenolpyruvate carboxylase and malic enzymes.

In a particular embodiment, the selected gene is deleted, all or in part, and does not encode a functional protein. The target gene may be inactivated in said bacterium or an ancestor thereof, by homologous recombination, gene replacement, or targeted mutagenesis, or any other technique known per se in the art. In a preferred embodiment, the gene is inactivated by deletion of at least part of said gene, which may be replaced by a heterologous nucleic acid (e.g., a selection marker). In a preferred embodiment, the bacterium of the present invention lacks a portion of said gene, preferably at least 100 consecutive nucleotides thereof, more preferably at least 200, 300, 400 or 500.

Compositions

A further aspect of the invention resides in the use of bacteria of the invention to make compositions with particular properties, such as antioxidant properties. Such compositions can be cosmetic compositions or nutritional compositions, including dietary supplements and nutraceutical compositions.

For example, a dietary supplement can be prepared, including bacteria of the invention, or extracts thereof, and/or compound(s) produced by such bacteria, to supplement the diet and to provide nutriments, such as vitamins, fatty acids or amino acids, that may be missing or may not be consumed in sufficient quantities in a person's diet.

In a particular embodiment, a dietary supplement of the invention contains bacteria producing reduced molecules, or extract thereof. Such dietary supplements can be proposed as pills comprising a bacterial extract powder of bacteria producing reduced molecules, alone or in combination with other components. Otherwise, the pills can contain purified reduced molecules, alone or in combination with other components.

In the context of the invention, cosmetic compositions, or beauty products, relate to compositions suitable for application on at least a part of the body, for cosmetic effects. Cosmetic compositions of the invention include lotions, such as hair lotion and aftershave lotion, skin creams, such as day cream, anti-wrinkle cream and moisturizing cream, or make-up, such as lipstick, etc.

For example, bacteria (or extracts thereof) producing reduced molecules are used as an active ingredient in an amount effective to act as an antioxidant agent. Cosmetic compositions of the invention can contain, in addition or instead of bacteria, purified reduced molecules.

Preferentially, the composition further comprises one or more cosmetically acceptable carriers or diluents.

Co-Cultures

A further aspect of the invention resides in microorganism co-cultures having improved properties. More specifically, the invention relates to co-cultures using *Deinococcus* bacteria of the invention, which co-cultures have improved NADPH-dependent enzymatic activities.

In a particular embodiment, the invention relates to a co-culture of at least two distinct microorganisms, wherein at least one of said microorganisms is a *Deinococcus* bacterium presenting a metabolic pathway ratio between pentose phosphate and glycolysis greater than 0.5, and preferably greater than 1, and at least one of said microorganisms is a prokaryotic or eukaryotic cell, and wherein said at least two microorganisms are symbiotic to each other. The prokaryotic or eukaryotic cell may be selected, e.g., from bacteria, yeasts, plant cells, fungi, and mammalian cells. Examples of yeasts include, without limitation, *Saccharomyces, Kluyveromyces, Schizosaccharomyces, Pichia*, etc. Examples of bacteria include *Deinococcus* bacteria, *Bacillus* sp., *E. Coli, Clostridium* sp., etc.

Two microorganisms are considered symbiotic to each other when each requires the other for its survival and growth.

Co-cultures of the invention may comprise more than 2 distinct microorganisms, such as 3 or 4.

Also, co-cultures may be simultaneous or sequential, preferably simultaneous.

In this regard, a specific object of the invention is a culture of at least two distinct microorganisms, wherein at least one of said microorganisms is a *Deinococcus* bacterium presenting a metabolic pathway ratio between pentose phosphate and glycolysis greater than 0.5, and at least one of said microorganisms is a yeast.

These co-cultures offer an improved range of enzymatic activities and represent valuable products for industrial processes.

Further aspects and advantages of the invention will be disclosed in the following examples, which should be considered as illustrative and do not limit the scope of this application.

EXAMPLES

A] Identification and Characterization of Bacteria Having a PP/G Ratio Superior to 0.5

Stress-resistant bacteria are isolated from an environmental sample by performing a UV treatment of 4 mJ/cm$^2$ for 30 seconds, repeated five times at an interval of 4 hours. The remaining living bacteria are selected. Among these, two *Deinococcus geothermalis* strains (DG01 and DG02) are identified as presenting a PP/G ratio of interest. More particularly, the DG01 strain presents a PP/G ratio of 4.26, and the DG02 strain presents a PP/G ratio of 1.27.

In the following, a method of measurement of the metabolic pathway ratio for these two isolated strains is presented. This method consists of a $^{13}$C metabolic flux analysis as described in Krömer et at.

Cultivations in the Parallel Bioreactor System for Flux Analyses

Chemostat cultivations were performed for *Deinococcus geothermalis* strains DG01 and DG02 in a 15-vessel reactor system. Medium No. 6 containing 10 g/L glucose was used both in the batch phase and in the chemostat phase. The medium was supplemented with 10-fold vitamin solution (vitamin content in the medium 10 µg/L). Cultivation volume was 200 ml. Agitation rate was 800 rpm and set point for pH was 7.0. 1M NaOH was used to control pH. All cultivations were aerated with ambient air. Three levels of flow rate were used: triplicate cultivations with both strains using 10 ml/min aeration, duplicate cultivations with both strains using 30 ml/min aeration and duplicate cultivations with both strains using 65 ml/min aeration. One vessel was not inoculated but was kept as a control.

Chemostat feed was started 24 hours after the inoculation. Feed rate was 6.0 ml/h for each vessel. This corresponds to a dilution rate of 0.03/h. Chemostat feed was changed to $^{13}$C-labeled feed after 283 hours (1 g/L universally $^{13}$C-labeled glucose, 9 g/L natural glucose). Samples of 150 mL were taken after 49 hours of starting the labeled glucose feed. Samples were centrifuged and cell pellets were frozen at −20° C. After harvesting the cells, chemostat cultivations were continued with the medium containing natural glucose.

Sample Preparation and NMR Spectroscopy for $^{13}$C Metabolic Flux Ratio Analysis Labeled cells, harvested from the chemostat cultivations above, were hydrolyzed with 6M HCl at 110° C. for 20 hours. In the hydrolysis cells are broken down and the proteins are hydrolyzed to free amino acids. 16 of the 20 proteinogenic amino acids remain intact; Asn, Gln, Cys and Trp are destroyed. Acid was removed by a rotary evaporator, washed with water and freeze-dried. For NMR analysis the evaporated samples were dissolved in 500 µl of D$_2$O. Due to residual HCl, pH remains below 1, as spectrometer equipped with CPQCI cryoprobe. Two HSQC spectra from each sample were recorded corresponding to the aliphatic and aromatic areas of the spectrum.

ReTrace Pathfinding for the Metabolic Model

The reconstruction of the pathways of central carbon metabolism and amino acid biosynthetic pathways from their precursors was performed with ReTrace. ReTrace is a recent computational pathway analysis method (Pitkänen E, Jouhten P, Rousu J: Inferring branching pathways in genome-scale metabolic networks with ReTrace, in press, *BMC Syst. Biol.,* 2009), which can be queried to discover branching metabolic pathways in a universal metabolic database. Specifically, ReTrace aims to find pathways which transfer as many atoms from source to target metabolites as possible. Atom mappings, which describe how atoms are transferred in a reaction from substrate to product metabolites, are defined in the RPAIR database, which is a subdatabase of KEGG.

SwissProt database was queried with *Deinococcus* orf's by blastp (Altschul S F, Madden T L, Schaffer A A, Zhang J, Zhang Z, Miller W, Lipman D J: Gapped BLAST and PSI-BLAST: a new generation of protein database search programs. *Nucleic Acids Res.* 1997, 25:3389-3402) with the following options:

Blastp-outfmt 6-query <input file name>-db swiss-out <output file name>

Each reaction in the KEGG database was assigned a score by taking the maximum BLAST score of all SwissProt-*Deinococcus* strain sequence pairs, where the SwissProt sequence had been annotated with an EC number corresponding to the reaction. Reaction scores reflected the degree of evidence from the detection of sequence homology that there exists an enzyme catalyzing the reaction in the strains of *Deinococcus*.

ReTrace was run with default settings with the reaction scores from the genome evidence. All reactions were considered bidirectional. To capture the paths in central carbon metabolism and in amino acid synthesis, ReTrace was run for several substrate and product metabolites.

Constructing the Metabolic Models

Stoichiometric metabolic models of central carbon metabolism were manually set up for *Deinococcus* strains DG01 and DG02 from the path-finding results. To generate gapless models some reactions were included with low or no support from the genome data. Prokaryotic genome-wide metabolic models of *Escherichia coli* and *Bacillus subtilis* were examined for modeling the electron transfer chain, oxidative phosphorylation and transport reactions since the path-finding does not support searching them. The stoichiometric models were augmented for example with annotation and scoring information.

Metabolic Flux Ratio Analysis

The software FCAL (R. W. Glaser; FCAL 2.3.1. Szyperski T, Glaser R W, Hochuli M, Fiaux J, Sauer U, Bailey J E, Wüthrick K: Bioreaction network topology and metabolic flux ratio analysis by biosynthetic fractional $^{13}$C labeling and two-dimensional NMR spectroscopy. *Metab. Eng.* 1999, 1: 189-197) was used for the integration of $^{13}$C-scalar fine structures of proteinogenic aliphatic and aromatic amino acid carbon signals in the $^1$H-$^{13}$C-HSQC NMR spectra of the sample containing the strain DG01 and the sample containing the strain DG02, and for the calculation of relative abundances of intact carbon fragments originating from a single source molecule of glucose.

The nomenclature used for the intact carbon fragments, fragmentomers, has been described by Szyperski (Biosynthetically directed fractional $^{13}C$-labelling of proteinogenic amino acids. An efficient tool to investigate intermediary metabolism. *Eur. J. Biochem.* 1995, 232: 433-448).

Fragmentomer information obtained from proteinogenic amino acids can be traced back to the metabolic intermediates in central carbon metabolism since the carbon backbones are conserved in the amino acid synthesis pathways. Mass balance equations of the specific carbon fragments of the metabolic intermediates were formulated from the propagated fragmentomer information for junctions in central carbon metabolism.

The upper bound for the fraction of phosphoenolpyruvate (Pep) from the pentose phosphate pathway (PPP) was calculated as described by Maaheimo and co-workers (Maaheimo H, Fiaux J, Gakar P Z, Bailey J E, Sauer U, Szyperski T: Central carbon metabolism of *Saccharomyces cerevisiae* explored by biosynthetic fractional $^{13}C$ labeling of common amino acids. *Eur. J. Biochem.* 2001, 268: 2464-2479). The fraction of Pep originating from phosphoenolpyruvate carboxykinase activity, denoted by $X_{PEPck}$, was calculated from the ratio of the fraction of Pep molecules containing an intact C1-C2 fragment and a cleaved bond between C2 and C3 and the fraction of oxaloacetate (Oaa) molecules containing the equivalent fragments. Phosphoenolpyruvate carboxykinase is assumed to be the only source of such molecules. Phe-C$\alpha$, Tyr-C$\alpha$ and Asp-C$\alpha$, Thr-C$\alpha$ can be traced back to the C2 of Pep and Oaa, respectively.

The contribution of the anaplerotic interconversion of Pep into Oaa, which participates in the TCA cycle, was also calculated. In the calculation of anaplerotic replenishment of the TCA cycle by synthesis of Oaa from Pep via the joint action of pyruvate kinase and pyruvate carboxylase, the condensation of AcCoA and Oaa is assumed to be irreversible. No hit for citrate lyase, catalysing the reaction in the opposite direction, was found in the genome evidence-supported path-finding. The Oaa molecules originating from oxoglutarate (Oga) through the TCA cycle possess cleaved C2-C3 bonds, allowing the measurement of the fraction of Oaa originating from anaplerotic carboxylation and the fraction of intact C2-C3 connectivities in Oaa. The intact fragments in Oaa were obtained from the intact fragments in Oga since the C2-C3-C4 fragment of Oaa is conserved in the TCA cycle in the synthesis of Oga. The intact fragments in biosynthetic precursor Oga were deduced from Glu.

The upper and lower bounds for pyruvate (Pyr) originating from the malic enzyme reaction, denoted by $X_{MAE\_ub}$ and $X_{MAE\_lb}$ respectively, were calculated from a mass balance of intact C2-C3 fragments of Pyr. The upper and lower bounds were obtained from the assumption that the substrate fragment for malic enzyme has an equally conserved connectivity as Oga and Oaa.

The skilled person can easily implement the method described above to identify and characterize further bacteria having a PP/G pathway ratio superior or equal to 0.5, from any sample comprising bacteria.

B] Production of Deinoxanthine

Deinoxanthine is a specific orange-red pigment, close to astaxanthin. Deinoxanthine is well-known to be a powerful antioxidant, immuno-stimulant and photo-protective compound.

In the following, the production of deinoxanthine, using the method of bioproduction of the invention with an isolated *Deinococcus radiodurans* (DR04), is described. The bacterium DR04 is identified and isolated according to the method described above. This bacterium presents a PP/G ratio superior to 0.5.

Materials and Methods:

Complex Medium Glucose contains: peptone 2 g/L, yeast extract (Lot BCBD0078V; Ref: 70161 Fluka) 5 g/L and glucose (Lot 080M0143V; Ref: 68270 SIGMA) 10 g/L in osmosed water: solution sterilized by autoclaving (15 minutes at 120° C.). To this solution are added the following solutions: MOPS buffer solution (10×) pH7 [acid MOPS 400 mM, $NH_4Cl$ 200 mM, NaOH 100 mM, KOH 100 mM, $CaCl_2$ 5 μM, $Na_2SO_4$ 2.76 mM, $MgCl_2$ 5.28 mM]; micronutrients (10000×) [$(NH_4)_6(Mo_7)$24 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; vitamins (10,000×) [10 mg/L of each: D-biotin, Niacin (nicotinic acid), Pyridoxin (pyroxidal hydrochloride) B6, Thiamin (vitamin B1 hydrochloride)—Stock pH4—filter sterilized (0.22 μm)]; $FeCl_3$ (100×) 2 mM in $C_6H_5Na_3O_7$ 20 mM filter sterilized (0.22 μm); $K_2HPO_4$ 100 g/L, autoclaved.

All solvents for high-performance liquid chromatography (HPLC) were super purity solvents purchased from Sigma Aldrich. 2,6-Di-r-butyl-p-cresol (BHT) in purum quality and NaB& in purum p.a. quality were purchased from Sigma Aldrich.

Bacteria and Culture Procedure

*Deinococcus* sp. were inoculated on Complex Medium Glucose. The bacteria were grown under aerobic conditions and continuous shaking at 45° C. or 30° C. during seven days. The culture reached its stationary phase and bacteria could be harvested by centrifugation. The average pellet weight was 5 g per liter of culture.

Extraction and Purification

A bacteria cell pellet of 500 mg was washed two times with 50 mL of ultra-pure H2O. Then the washed bacteria cell pellet was mixed with 1 ml of methanol containing 1% of BHT as an antioxidant under argon, homogenized for 10 minutes and then centrifuged. The pellet was reextracted three times until it turned totally colorless. The extracts were combined.

LCMS Studies

The crude material was purified by a Hypersil ODS (4.6×250 mm, 5 μm) column, on a Dionex HPLC system using a mix of acetonitrile/methanol/isopropanol (40/50/10) (v/v) as mobile phase, a flow rate of 0.8 ml/min, and the detector set at 480 nm.

HPLC assay of deinoxanthine in an extract of DR04 was used to assess the amount of deinoxanthine produced by the bacterium. It can be expressed as mg/g of dry biomass.

Results

The amount of deinoxanthine contained in the extract of DR04 was 0.1 mg/g dry biomass.

Such extract can be used advantageously to prepare a cosmetic composition and/or a dietary supplement, with antioxidant properties.

C] Production of Carotenoids

Carotenoids are organic pigments produced by some bacteria to protect themselves from oxidative attack. Carotenoids, well-known to be powerful antioxidant compounds, cannot be manufactured by mammals, so they obtain carotenoids in their diets. Mammals employ carotenoids in various ways in their metabolisms.

In the following, the production of carotenoids, using the method of bioproduction of the invention with an isolated *Deinococcus geothermalis* (MX6-1E_14), is described.

More precisely, carotenoids are produced using *Deinococcus* cells cultivated on a culture medium containing either glucose or xylose as the sole carbon source. The *Deinococcus* cells have been previously identified and isolated according to the method described above. These bacteria present a PP/G ratio superior to 0.5.

Material and Methods:

Medium No. 6 Composition:

Reducing sugar (20 g/L); MOPS acid 40 mM; $NH_4Cl$ 30 mM; NaOH 10 mM; KOH 10 mM; $CaCl_2.2H_2O$ 2 µM; $Na_2SO4.10H_2O$ 0.1 mM; $MgCl_2.6H_2O$ 0.1 mM; $(NH_4)_6(Mo_7)O_{24}.4H_2O$ 10 nM; $H_3BO_3$ 100 nM; $CoCl_2.6H_2O$ 10 nM; $CuSO_4.5H_2O$ 200 nM; $MnCl_2$ 1 µM; $ZnSO_4.7H_2O$ 100 nM; D-Biotin 10 µg/L; Niacin (nicotinic acid) 10 µg/L; Pyridoxin (pyridoxal HCl or vitamin B6) 10 µg/L; Thiamin HCl (vitamin B1) 10 µg/L; vitamin B12 10 µg/L; $FeCl_3$ 200 µM; Sodium Citrate.$2H_2O$ 200 µM; $K_2HPO_4$ 0.5 g/L.

Bacteria and Culture Procedure:

*Deinococcus* strain MX6-1E 14 was cultivated in 500 ml medium No. 6 containing either 20 g/l of glucose or 20 g/l of xylose in 1 L fermentor at 45° C. under 0.1 L/min of aeration.

Extraction and Purification:

Carotenoid extraction was performed as follows:
- the bacteria were harvested at the stationary phase and centrifuged at 400 rpm;
- 10 mg of pellets were taken in 1 ml of methanol and vortexed 3 min;
- the sample was then centrifuged 3 min at 10,000 rpm at 4° C.;
- the supernatant was recovered and absorbance measured at 540 nm to quantify the carotenoids (the amount of carotenoids is proportional to the absorbance at 540 nm).

Results

In the *Deinococcus* strain used in the experiment, about 50% of the glucose is metabolized by glycolysis and 50% by pentose phosphate pathway. This bacterium generates a NADH/NADPH ratio of 1, which is optimal for the production of carotenoids.

Extraction from glucose culture medium: $OD_{540nm}=0.042$

Extraction from xylose culture medium: $OD_{540nm}=0.012$

In the xylose culture medium the NADH/NADPH ratio is modified in favor of NADH (i.e., xylose generates only NADH), and the production of carotenoids is decreased compared to the production of carotenoids using the same strain in the glucose culture medium, wherein the NADH/NADPH ratio remains equal to 1.

D] Recombinant Bacterium: Insertion of an NADP-Dependent ADH Encoding Gene

The metabolic flux ratio analysis above shows that in the DG02 strain up to 56% of the glucose is consumed through the pentose phosphate pathway, indicating that an important part of NADPH is produced as redox potential. In order to use this NADPH pool for ethanol production, an NADP-dependent ADH-encoding gene from *Moorella* sp. HUC 22-1 (SEQ ID NO: 3) is introduced into the chromosome of strain DG02.

Materials and Methods

Bacterial Strains and Growth Conditions:

*Escherichia coli* (*E. coli*) strain SCS110 is used to propagate plasmids. The bacteria are cultivated at 37° C. and 200 RPM in Luria-Bertani (LB) Broth (per liter: Tryptone 10 g, Yeast extract 5 g, Sodium chloride 10 g). Solid media is prepared by addition of Agar 1.5%.

*Deinococcus* bacteria DG02 are cultivated at 45° C. and 200 RPM in PGY. The composition of the PGY medium is as follows, per liter: Peptone (10 g), Yeast extract (5 g) and Glucose (1 g). Composition of the solid media is, per liter: Peptone (10 g), Yeast extract (5 g), Glucose (1 g) and Agar (15 g).

Transformation:

*E. coli* transformation is done using commercial competent cells SCS110 from Stratagene or JM109 from Promega.

For *Deinococcus* cells, a fresh culture in stationary phase is diluted 100 times in 50 ml of PGY. Cells are grown until late exponential phase ($OD_{600nm}=0.8$); the pellet is resuspended in an appropriate volume of ice-cold 2×PGY/10% v/v Glycerol/30 mM $CaCl_2$. For transformation, the desired amount of plasmid DNA is added to 100 µl of the cells. The mixture is incubated 30 minutes on ice transferred at 42° C. for 90 seconds and back to ice for 5 minutes. 200µl of fresh 2×PGY medium is added and the transformants are shaken at 200 RPM and 37° C. during 2 hours. They are serially diluted and spread on appropriate selective PGY plates.

DNA Manipulation:

Plasmid minipreparation from *E. coli* cells is done using the QIAGEN miniprep DNA purification system and midipreparation is done using the Plasmid DNA purification NUCLEOBOND Xtra Midi Plus EF kit from Macherey-Nagel. These preparations are done from 3-100 ml of *E. coli* culture in stationary phase.

The oligonucleotides are synthesized by Eurogentec. The polymerases used for PCR amplification are the PHUSION Hi-Fidelity polymerase from Finzyme and the KOD Xtreme-hot start DNA polymerase from Novagen for overlapping PCRs. PCR fragments are cleaned up using the Wizard SV Gel and PCR Clean-Up System kit from Promega.

Genetic materials are separated by agarose gel electrophoresis. DNA is quantified with a BioPhotometer from Eppendorf.

DNA inserts are synthesized by Genecust Europe and cloned into appropriate vector.

Method of Genetic Insertion into *Deinococcus* Chromosome:

Insertion of DNA fragments into the chromosome of DG02 is performed using the homologous recombination mechanism. The cassette of insertion contains an operon with the alcohol dehydrogenase encoding gene ($adh_{Zm}$) from *Z. mobilis*, placed under the control of the pgroESL promoter, and a pTufA-bleo bleocin resistance cassette. The DNA sequence of the region that has to be inserted is flanked by 500 bp regions homologous to the sequences upstream or downstream of the chromosomic target. The insertion cassette is carried by pMD66 thermosensitive shuttle vector transformed into *Deinococcus* and high temperature exposure (52° C. for 4 days) is used to allow for chromosomic insertion and plasmid loss.

The transformants that have incorporated the region of interest into the chromosome (named DG03) are selected on PGY medium containing bleocin.

Correct insertions are checked by PCR on genomic DNA, and sequencing of the modified chromosome on the region of interest.

Alcohol Dehydrogenase Activity Test:

4 ml of pararosaniline (Sigma) at 2.5 mg/ml in absolute ethanol are added to 200 ml of LB agar containing 50 mg of sodium bisulfite (Conway et al, 1987b). 2-day-old DG03 cells grown on TGY agar plates (supplemented if necessary with bleocin) are plated on the indicator plates and incubated at 37° C. for 2 to 3 hours.

Ethanol Production:

The ability of DG03 to produce ethanol from whole wheat 3%- or 6%-containing medium in aerobic conditions is evaluated. The test is carried out at 30° C.

Pre-cultures (in stationary phase) are prepared in complex medium glucose [peptone 2 g/L, yeast extract 5 g/L and glucose 10 g/L in osmosed water; solution sterilized by autoclaving (15 minutes at 120° C.)]. To this solution are added the following solutions: MOPS buffer solution (10×) pH7 [acid MOPS 400 mM, $NH_4Cl$ 200 mM, NaOH 100 mM, KOH 100 mM, $CaCl_2$ 5 µM, $Na_2SO_4$ 2.76 mM, $MgCl_2$ 5.28 mM]; micronutrients (10000×) [$(NH_4)_6(Mo_7)24$ 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; and $FeCl_3$ (100×) 2 mM in $C_6H_5Na_3O_7$ 20 mM; $K_2HPO_4$ 1 g/L: solutions sterilized by filtration (0.2 µm). 6 ml of enriched medium [carbon source 10 g/L in osmosed water; solution sterilized by autoclaving (15 minutes at 120° C.)] are seeded (seeding at 1% v/v).

Bleocin (3 µg/mL of the culture medium) is added to this culture medium before the seeding.

Gas Chromatography FID analysis (Varian CP-WAX 57 CB 25 m*0.32 mm column) is used to quantify ethanol. Residual glucose is quantified by HPLC coupled with refractometry (Phenomenex LUNA 3 µm $NH_2$ 100 A 150*4.6 mm column, acetonitrile/$H_2O$ 85:15 mobile phase).

Ethanol production is monitored after 7 days of growth in whole wheat 3%- or 6%-containing medium, in aerobic conditions (i.e., cultures are left in an incubator, at 30° C., under agitation, for 7 days. The cultures are then centrifuged for 10 minutes at 4000 rpm. Supernatants are filtered (0.2 µm), poured into other tubes, and placed at −80° C.).

The expression of the NADP-dependent ADH (SEQ ID NO. 5) maximizes ethanol production by the DG03 bacteria.

---

The invention claimed is:

1. An isolated *Deinococcus* bacterium, wherein said *Deinococcus* bacterium has a metabolic pathway ratio of pentose phosphate over glycolysis between 1 and 20 during the exponential phase of growth when cultured in a medium comprising glucose.

2. The isolated *Deinococcus* bacterium of claim 1, wherein the metabolic pathway ratio of pentose phosphate over glycolysis is between 2 and 20.

3. The isolated *Deinococcus* bacterium of claim 1, said *Deinococcus* bacterium being obtained by a method comprising the following steps:
   a) providing a sample comprising the *Deinococcus* bacteria;
   b) subjecting the sample to a cell-destructing DNA damaging treatment;
   c) identifying or isolating living or growing *Deinococcus* bacteria from said treated sample;
   d) measuring the metabolic pathway ratio of pentose phosphate over glycolysis of said *Deinococcus* bacteria of step c); and
   e) selecting a *Deinococcus* bacterium of step d) which has a metabolic pathway ratio of pentose phosphate over glycolysis between 1 and 20 during the exponential phase of growth when cultured in a medium comprising glucose.

4. The isolated *Deinococcus* bacterium of claim 1, wherein said *Deinococcus* bacterium can utilize lignin, cellulose, hemi-cellulose, starch, xylan, polysaccharide, xylose, galactose, sucrose, lactose, glycerol, molasses or glucose, or derivatives thereof, as a carbon source.

5. The isolated *Deinococcus* bacterium of claim 1, said *Deinococcus* bacterium further comprising at least one recombinant nucleic acid sequence encoding an NADPH-dependent enzyme.

6. The isolated *Deinococcus* bacterium of claim 5, wherein said at least one recombinant nucleic acid sequence encodes an NADPH-dependent Alcohol dehydrogenase and/or an NADPH-dependent cytochrome P450.

7. A co-culture of at least two distinct microorganisms, wherein at least one of said microorganisms is the isolated *Deinococcus* bacterium according to claim 1 and at least one of said microorganisms is a prokaryotic or eukaryotic cell and wherein said at least two microorganisms are symbiotic to each other.

8. A dietary supplement comprising the isolated *Deinococcus* bacterium according to claim 1.

9. A cosmetic composition comprising the isolated *Deinococcus* bacterium according to claim 1.

10. A method of producing a compound of interest, the method comprising the steps of: contacting, in a reactor, a substrate with a *Deinococcus* bacterium to produce said compound of interest and recovering said compound of interest, wherein said *Deinococcus* bacterium has a metabolic pathway ratio of pentose phosphate over glycolysis between 1 and 20 during the exponential phase of growth when cultured in a medium comprising glucose.

11. The method of claim 10, wherein the compound of interest is a metabolite selected from alcohols, acids, amino acids, vitamins, sterols, flavonoids, fatty acids, isoprenoids, and polyols.

12. The method of claim 10, wherein the compound of interest is a pharmaceutical compound or nutrient selected from a protein, polypeptide, peptide, chemical compound, lipid, or saccharide, having a biological activity.

13. The method of claim 10, wherein the substrate is an aliphatic compound and the compound of interest is a dicarboxylic acid.

14. The method of claim 10, wherein said compound of interest is an antioxidant or reduced molecule.

15. The method of claim 14, wherein the antioxidant is selected from glutathione, deinoxanthine, vitamin C or E, an antioxidant enzyme, catalase, peroxidase or superoxide dismutase.

16. The method of claim 10, wherein the compound of interest is a carotenoid.

17. A method for the production of a compound of interest, the method comprising the steps of: selecting a *Deinococcus* bacterium which produces said compound, culturing, in a reactor, said *Deinococcus* bacterium in an appropriate culture medium comprising a source of carbon, and recovering the compound of interest from the *Deinococcus* bacterial extract or the culture medium thereof, wherein said *Deinococcus* bacterium has a metabolic pathway ratio of pentose phosphate over glycolysis between 1 and 20 during the exponential phase of growth when cultured in a medium comprising glucose.

18. A method for the bioconversion of a substrate into a substance of interest, the method comprising the steps of: selecting a *Deinococcus* bacterium having said bioconversion activity, culturing, in a reactor, said *Deinococcus* bacterium in an appropriate culture medium comprising a source of carbon and the substrate(s), and recovering the substance of interest from the *Deinococcus* bacterial extract or the culture medium thereof, wherein said *Deinococcus* bacterium has a metabolic pathway ratio of pentose phosphate over glycolysis between 1 and 20 during the exponential phase of growth when cultured in a medium comprising glucose.

19. The method of claim 18, wherein the substrate is an aliphatic compound and the substance of interest is a dicarboxylic acid.

20. A method for the production of a reduced molecule, the method comprising the steps of: selecting a *Deinococcus* bacterium which produces said reduced molecule, culturing, in a reactor, said *Deinococcus* bacterium in an appropriate culture medium comprising a source of carbon, and recovering the reduced molecule of interest from the *Deinococcus* bacterial extract or the culture medium thereof, wherein said *Deinococcus* bacterium has a metabolic pathway ratio of pentose phosphate over glycolysis between 1 and 20 during the exponential phase of growth when cultured in a medium comprising glucose.

21. A method for the production of a dietary supplement, the method comprising the steps of: selecting a *Deinococcus* bacterium that produces a reduced molecule, culturing, in a reactor, said *Deinococcus* bacterium in an appropriate culture medium comprising a source of carbon, recovering the reduced molecule of interest from the *Deinococcus* bacterial extract or the culture medium thereof, and producing the dietary supplement using said reduced molecule as an active ingredient, wherein the *Deinococcus* bacterium has a metabolic pathway ratio of pentose phosphate over glycolysis between 1 and 20 during the exponential phase of growth when cultured in a medium comprising glucose.

22. A method for the production of a cosmetic composition, the method comprising the steps of: selecting a *Deinococcus* bacterium which produces a reduced molecule, culturing, in a reactor, said *Deinococcus* bacterium in an appropriate culture medium comprising a source of carbon, recovering the reduced molecule of interest from the *Deinococcus* bacterial extract or the culture medium thereof, and producing the cosmetic composition using said reduced molecule as an active ingredient, wherein the *Deinococcus* bacterium has a metabolic pathway ratio of pentose phosphate over glycolysis between 1 and 20 during the exponential phase of growth when cultured in a medium comprising glucose and wherein the method is performed in a reactor.

* * * * *

SEQUENCE LISTING

```
<160> NUMBER OF SEQ ID NOS: 5

<210> SEQ ID NO 1
<211> LENGTH: 23
<212> TYPE: DNA
<213> ORGANISM: artificial
<220> FEATURE:
<223> OTHER INFORMATION: primer

<400> SEQUENCE: 1
gttacccgga atcactgggc gta                                           23

<210> SEQ ID NO 2
<211> LENGTH: 23
<212> TYPE: DNA
<213> ORGANISM: artificial
<220> FEATURE:
<223> OTHER INFORMATION: primer

<400> SEQUENCE: 2
ggtatctacg cattccaccg cta                                           23

<210> SEQ ID NO 3
<211> LENGTH: 876
<212> TYPE: DNA
<213> ORGANISM: Moorella sp

<400> SEQUENCE: 3
atggacaagg taaaagtggc tgttatcggc ccgggcaata tcgggtccga cctgatgtac     60
aagatcctgc gcagccggca tctagagatg gccctgatga ccgtattat cgaatccgag    120 ggcatcaagc gggccaggaa gctgggtatc aagacatcca tcgaaggtgt caaggccgtc   180
ctggcggaag acgatatcaa gattgtcttt gacgccaccg gggccaaacc ccacttacag   240
catgcgccgc ttttaaaaga agcgggcaag atcgccatcg acttgacacc ggcggcagta   300
ggtccctacg tggtacccctg tgtcaacctg gaccaggtta aggccgaacc aaaccttaac   360
atggtcacct gcggtggcca ggctacagta cccatcgtct atgccatcaa ccgggtggcc   420
ggggccagat acgctgagat tgtagcctgc atcgcttcca agagcgccgg gccggggacc   480
cgccagaaca ttgacgagtt cacccagact acggccaagg ccctggaggt tgtcggcggg   540
gcgaagaagg gcaaagccat cattattctg aatcctgccg agccaccat tatgatgcat   600 aacaccattt atgtagaggt cgaaaagccc gacatcgaag ccattcgcgc ttcggttgaa   660
gccatggtca aggaaatcca gagctatgtt cccgggtacc ggctcgtcgt gccgcccatt   720
```

| | | | | |
|---|---|---|---|---|
| cttgacggca | acaaagtaac | ggcagctgtt | gaagtggagg gtgctggtga | cttcctgccc | 780 |
| aaatactccg | gtaatctgga | tattatcact | tcagcagccg tggcggtagc | tgaaaagctg | 840 |
| gcccaggaac | tgcaggtaaa | ggaagggta | gcatga | | 876 |

<210> SEQ ID NO 4
<211> LENGTH: 4957
<212> TYPE: DNA
<213> ORGANISM: Bacillus megaterium

<400> SEQUENCE: 4

| | | | | | |
|---|---|---|---|---|---|
| agatctttat | gaagacatag | ctgcagaaga | aaaagcaaga | gctacatatc | aatggttaat | 60 |
| tgatatatca | gatgatcccg | atttaaacga | cagcttacga | ttttacgag | aaagagagat | 120 |
| tgttcactca | cagcggttcc | gcgaggccgt | ggagatttta | aaagatgaca | gagacaggaa | 180 |
| gaaaatcttt | taactagtaa | aaaaacatcc | cccttggcga | atgcaaacga | aaggagggat | 240 |
| gttttttgtt | gtgactgcgt | tgattatgcg | ctagaactgc | agtgacaaga | aacaaccttt | 300 |
| aatttccctt | caacatcttt | ccaaactcgc | gtataactgt | attcacctcc | aatagattca | 360 |
| ccggttgcca | gtgccccatt | taacgctact | tttgtaacgg | taacggcaag | ttcttgaaac | 420 |
| agtttaactt | cttgttccaa | cacttccatg | cccgctatat | caagactttt | tgaacgatga | 480 |
| acatttatat | cttcttcttt | tgacaaccat | tgcccaaggt | gattcacaaa | aataagctca | 540 |
| tctgaaagta | attcttctaa | tagctctatg | ttattagaaa | gcatggctga | gcgaagcatt | 600 |
| tcttcgtatt | ctataactct | tgcttgattc | attttaatc | ctcctttacg | ccttgtgtaa | 660 |
| ctctttttcta | tttccacgtt | gcttttcctt | taaacttctt | tcattaataa | ttcgtgctaa | 720 |
| attatgttaa | tagaggggat | aagtggacta | attttctgta | agcactaaat | attctgaaat | 780 |
| actctgttaa | ttacctttaa | atggtataaa | attagaatga | agaaccttt | tctttccact | 840 |
| tttctagtta | tcttttttact | attaagatgc | agttttttat | acttgtaatt | gtagcggaat | 900 |
| gaacgttcat | tccgttttttg | aaaagaggtg | ataaagtgga | atctactcca | acaaaacaaa | 960 |
| aagcgatttt | ttctgcttcg | cttctgctgt | ttgcagaaag | agggtttgat | gcaaccacga | 1020 |
| tgccaatgat | tgcagagaat | gccaaagtag | agcaggaac | aattatcgc | tactttaaaa | 1080 |
| ataaagaaag | ccttgtaaat | gaattattcc | aacagcacgt | aaacgagttt | ttacagtgca | 1140 |
| ttgaaagcgg | tctggcaaac | gagagagatg | gataccgaga | tgggtttcat | catatctttg | 1200 |
| aaggtatggt | gacatttact | aaaaaccatc | ctcgtgctct | tggatttatt | aaaactcata | 1260 |
| gccaaggaac | tttttttaaca | aagagagcc | gcttagcata | tcaaaagctg | gtggaatttg | 1320 |
| tttgtacgtt | cttcagagaa | ggacaaaagc | aaggtgtgat | tagaaatctt | cctgaaaatg | 1380 |
| cgctaattgc | tattttattt | ggaagtttca | tggaagtata | tgaaatgatt | gaaaatgact | 1440 |
| acttatcttt | aactgatgaa | cttcttaccg | gtgtagaaga | gagtctgtgg | gcagcactta | 1500 |
| gcagacaatc | atgaaactta | acaagtgaaa | gagggataac | atgacaatta | agaaatgcc | 1560 |
| tcagccaaaa | acgtttggag | agcttaaaaa | tttaccgtta | ttaaacacag | ataaaccggt | 1620 |
| tcaagctttg | atgaaaattg | cggatgaatt | aggagaaatc | tttaaattcg | aggcgcctgg | 1680 |
| tcgtgtaacg | cgctacttat | caagtcagcg | tctaattaaa | gaagcatgcg | atgaatcacg | 1740 |
| ctttgataaa | aacttaagtc | aagcgcttaa | atttgtacgt | gattttgcag | gagacgggtt | 1800 |
| atttacaagc | tggacgcatg | aaaaaaattg | gaaaaagcg | cataatatct | tacttccaag | 1860 |
| cttcagtcag | caggcaatga | aaggctatca | tgcgatgatg | gtcgatatcg | ccgtgcagct | 1920 |

```
tgttcaaaag tgggagcgtc taaatgcaga tgagcatatt gaagtaccgg aagacatgac    1980
acgtttaacg cttgatacaa ttggtctttg cggctttaac tatcgcttta acagctttta    2040
ccgagatcag cctcatccat ttattacaag tatggtccgt gcactggatg aagcaatgaa    2100
caagctgcag cgagcaaatc cagacgaccc agcttatgat gaaaacaagc gccagtttca    2160
agaagatatc aaggtgatga acgacctagt agataaaatt attgcagatc gcaaagcaag    2220
cggtgaacaa agcgatgatt tattaacgca tatgctaaac ggaaaagatc cagaaacggg    2280
tgagccgctt gatgacgaga acattcgcta tcaaattatt acattcttaa ttgcgggaca    2340
cgaaacaaca agtggtcttt tatcatttgc gctgtatttc ttagtgaaaa atccacatgt    2400
attacaaaaa gcagcagaag aagcagcacg agttctagta gatcctgttc caagctacaa    2460
acaagtcaaa cagcttaaat atgtcggcat ggtcttaaac gaagcgctgc gcttatggcc    2520
aactgctcct gcgttttccc tatatgcaaa agaagatacg gtgcttggag gagaatatcc    2580
tttagaaaaa ggcgacgaac taatggttct gattcctcag cttcaccgtg ataaaacaat    2640
ttggggagac gatgtggaag agttccgtcc agagcgtttt gaaaatccaa gtgcgattcc    2700
gcagcatgcg tttaaaccgt ttggaaacgg tcagcgtgcg tgtatcggtc agcagttcgc    2760
tcttcatgaa gcaacgctgg tacttggtat gatgctaaaa cactttgact ttgaagatca    2820
tacaaactac gagctggata ttaaagaaac tttaacgtta aaacctgaag gctttgtggt    2880
aaaagcaaaa tcgaaaaaaa ttccgcttgg cggtattcct tcacctagca ctgaacagtc    2940
tgctaaaaaa gtacgcaaaa aggcagaaaa cgctcataat acgccgctgc ttgtgctata    3000
cggttcaaat atgggaacag ctgaaggaac ggcgcgtgat ttagcagata ttgcaatgag    3060
caaaggattt gcaccgcagg tcgcaacgct tgattcacac gccggaaatc ttccgcgcga    3120
aggagctgta ttaattgtaa cggcgtctta taacggtcat ccgcctgata acgcaaagca    3180
atttgtcgac tggttagacc aagcgtctgc tgatgaagta aaaggcgttc gctactccgt    3240
atttggatgc ggcgataaaa actgggctac tacgtatcaa aaagtgcctg cttttatcga    3300
tgaaacgctt gccgctaaag gggcagaaaa catcgctgac cgcggtgaag cagatgcaag    3360
cgacgacttt gaaggcacat atgaagaatg gcgtgaacat atgtggagtg acgtagcagc    3420
ctactttaac ctcgacattg aaaacagtga agataataaa tctactcttt cacttcaatt    3480
tgtcgacagc gccgcggata tgccgcttgc gaaaatgcac ggtgcgtttt caacgaacgt    3540
cgtagcaagc aaagaacttc aacagccagg cagtgcacga agcacgcgac atcttgaaat    3600
tgaacttcca aaagaagctt cttatcaaga aggagatcat ttaggtgtta ttcctcgcaa    3660
ctatgaagga atagtaaacc gtgtaacagc aaggttcggc ctagatgcat cacagcaaat    3720
ccgtctggaa gcagaagaag aaaaattagc tcatttgcca ctcgctaaaa cagtatccgt    3780
agaagagctt ctgcaatacg tggagcttca agatcctgtt acgcgcacgc agcttcgcgc    3840
aatggctgct aaaacggtct gcccgccgca taaagtagag cttgaagcct tgcttgaaaa    3900
gcaagcctac aaagaacaag tgctggcaaa acgtttaaca atgcttgaac tgcttgaaaa    3960
atacccggcg tgtgaaatga attcagcga atttatcgcc cttctgccaa gcatacgccc    4020
gcgctattac tcgatttctt catcacctcg tgtcgatgaa aaacaagcaa gcatcacggt    4080
cagcgttgtc tcaggagaag cgtggagcgg atatggagaa tataaaggaa ttgcgtcgaa    4140
ctatcttgcc gagctgcaag aaggagatac gattacgtgc tttatttcca caccgcagtc    4200
agaatttacg ctgccaaaag accctgaaac gccgcttatc atggtcggac cgggaacagg    4260
cgtcgcgccg tttagaggct tgtgcaggc gcgcaaacag ctaaaagaac aaggacagtc    4320
```

```
acttggagaa gcacatttat acttcggctg ccgttcacct catgaagact atctgtatca    4380
agaagagctt gaaaacgccc aaagcgaagg catcattacg cttcataccg ctttttctcg    4440
catgccaaat cagccgaaaa catacgttca gcacgtaatg gaacaagacg gcaagaaatt    4500
gattgaactt cttgatcaag gagcgcactt ctatatttgc ggagacggaa gccaaatggc    4560
acctgccgtt gaagcaacgc ttatgaaaag ctatgctgac gttcaccaag tgagtgaagc    4620
agacgctcgc ttatggctgc agcagctaga agaaaaaggc cgatacgcaa agacgtgtg    4680
ggctgggtaa attaaaaaga ggctaggata aaagtagttt agttggttga aggaagatcc    4740
gaacgatgaa tcgttcggat ctttttattg gtagagtaaa cgtagatttc atctatttag    4800
tgacttgtag cggttgattg gagggcaagg tgaagactcc aatcaaccgc ggtgtcacat    4860
gcaagccata cgaaattcat ttctcccatt tattcgtctt ttgtcccac ttaattttta     4920
tagcgcctta acgtttcttc tgcgtgacag cagatct                             4957
```

<210> SEQ ID NO 5
<211> LENGTH: 291
<212> TYPE: PRT
<213> ORGANISM: Moorella sp

<400> SEQUENCE: 5

```
Leu Ala Glu Asp Asp Ile Lys Ile Val Phe Asp Ala Thr Gly Ala Lys
1               5                   10                  15

Pro His Leu Gln His Ala Pro Leu Leu Lys Glu Ala Gly Lys Ile Ala
            20                  25                  30

Ile Asp Leu Thr Pro Ala Ala Val Gly Pro Tyr Val Pro Cys Val
        35                  40                  45

Asn Leu Asp Gln Val Lys Ala Glu Pro Asn Leu Asn Met Asp Lys Val
    50                  55                  60

Lys Val Ala Val Ile Gly Pro Gly Asn Ile Gly Ser Asp Leu Met Tyr
65                  70                  75                  80

Lys Ile Leu Arg Ser Arg His Leu Glu Met Ala Leu Met Thr Gly Ile
                85                  90                  95

Ile Glu Ser Glu Gly Ile Lys Arg Ala Arg Lys Leu Gly Ile Lys Thr
            100                 105                 110

Ser Ile Glu Gly Val Lys Ala Val Met Val Thr Cys Gly Gly Gln Ala
        115                 120                 125

Thr Val Pro Ile Val Tyr Ala Ile Asn Arg Val Ala Gly Ala Arg Tyr
    130                 135                 140

Ala Glu Ile Val Ala Cys Ile Ala Ser Lys Ser Ala Gly Pro Gly Thr
145                 150                 155                 160

Arg Gln Asn Ile Asp Glu Phe Thr Gln Thr Thr Ala Lys Ala Leu Glu
                165                 170                 175

Val Val Gly Gly Ala Lys Lys Gly Lys Ala Ile Ile Leu Asn Pro
            180                 185                 190

Ala Glu Pro Pro Ile Met Met His Asn Thr Ile Tyr Val Glu Val Glu
        195                 200                 205

Lys Pro Asp Ile Glu Ala Ile Arg Ala Ser Val Glu Ala Met Val Lys
    210                 215                 220

Glu Ile Gln Ser Tyr Val Pro Gly Tyr Arg Leu Val Val Pro Pro Ile
225                 230                 235                 240

Leu Asp Gly Asn Lys Val Thr Ala Ala Val Glu Val Glu Gly Ala Gly
                245                 250                 255
```

```
Asp Phe Leu Pro Lys Tyr Ser Gly Asn Leu Asp Ile Ile Thr Ser Ala
        260                 265                 270

Ala Val Ala Val Ala Glu Lys Leu Ala Gln Glu Leu Gln Val Lys Glu
        275                 280                 285

Gly Val Ala
    290
```

UNITED STATES PATENT AND TRADEMARK OFFICE
CERTIFICATE OF CORRECTION

PATENT NO. : 9,574,198 B2  
APPLICATION NO. : 14/366333  
DATED : February 21, 2017  
INVENTOR(S) : Jean-Paul Leonetti, Juha-Pekka Pitkanen and Paula Jouhten It is certified that error appears in the above-identified patent and that said Letters Patent is hereby corrected as shown below:

In the Specification

Column 15,  
Line 33, "et at." should read --et al.--.

Column 19,  
Line 19, "MX6-1E 14" should read --MX6-1E_14--.

Signed and Sealed this  
First Day of August, 2017

Joseph Matal  
*Performing the Functions and Duties of the*  
*Under Secretary of Commerce for Intellectual Property and*  
*Director of the United States Patent and Trademark Office*